United States Patent
Parikh et al.

(10) Patent No.: US 12,109,188 B1
(45) Date of Patent: Oct. 8, 2024

(54) LIQUID PHARMACEUTICAL FORMULATIONS OF TOPIRAMATE

(71) Applicant: TaP Pharmaceuticals AG, Baar (CH)

(72) Inventors: Nilesh Parikh, Irvine, CA (US); William Hite, Winchester, CA (US)

( * ) Notice: Subject to any disclaimer, the term of this patent is extended or adjusted under 35 U.S.C. 154(b) by 0 days.

(21) Appl. No.: 18/126,221

(22) Filed: Mar. 24, 2023

(51) Int. Cl.
 *A61K 31/36* (2006.01)
 *A61K 9/00* (2006.01)
 *A61K 47/10* (2017.01)

(52) U.S. Cl.
 CPC ............ *A61K 31/36* (2013.01); *A61K 9/0053* (2013.01); *A61K 47/10* (2013.01)

(58) Field of Classification Search
 None
 See application file for complete search history.

(56) References Cited

U.S. PATENT DOCUMENTS

| | | |
|---|---|---|
| 6,294,192 B1 | 9/2001 | Patel et al. |
| 11,197,823 B2 | 12/2021 | Sudhakar et al. |
| 11,197,825 B2 | 12/2021 | Sudhakar et al. |
| 2006/0270611 A1 | 11/2006 | Dries et al. |
| 2021/0169844 A1 | 6/2021 | Tu et al. |

FOREIGN PATENT DOCUMENTS

| | | |
|---|---|---|
| GB | 2594242 A | 10/2021 |
| WO | 2020053662 A2 | 3/2020 |

OTHER PUBLICATIONS

OpenWetWare, Glycerol, https://openwetware.org/wiki/Glycerol, retrieved May 30, 2023.*
Ma et al., Polyethylene glycol 400 (PEG400) affects the systemic exposure of oral drugs based on multiple mechanisms: taking berberine as an example, RSC Adv., 2017, 7, pp. 2435-2442 (Year: 2017).*
Paramar et al. "HPTLC Method for Estimation of Topiramate in Solubility Studies, Diffusion Studies, Plasma, Brain Homogenate and Pharmaceutical Formulation", Journal of Chromatographic Science, 2016, vol. 54, No. 7, 1105-1114.
Azurity Pharmaceuticals, Inc. Eprontia package insert.

* cited by examiner

*Primary Examiner* — David J Blanchard
*Assistant Examiner* — Edwin Coleman Mitchell

(57) ABSTRACT

Certain embodiments of the present disclosure provide liquid pharmaceutical formulations, suitable for oral administration, that contain a therapeutically effective amount of topiramate that is from 50 mg/ml to 100 mg/ml and amounts of polyethylene glycol ("PEG") 400 and glycerol sufficient to result in a greater than a prior art taught calculated maximum amount of the topiramate being in the solution phase of the formulation, at room temperature.

20 Claims, No Drawings

LIQUID PHARMACEUTICAL FORMULATIONS OF TOPIRAMATE

FIELD

The instant disclosure provides liquid pharmaceutical formulations, suitable for oral administration, that comprise topiramate and that exhibit advantageous solubility properties, and methods of making and using same.

BACKGROUND

Carbonic anhydrase inhibitors have a variety of established clinical uses, such as in treatment of glaucoma, altitude sickness, ulcers, idiopathic intracranial hypertension, osteoporosis, type II diabetes, tobacco dependence, obesity, eating disorders (e.g., binge eating and antipsychotic-induced weight gain), and neurological disorders (e.g., depression, mania, bipolar disorder, and borderline personality disorder) and as a diuretic and antiepileptic. Carbonic anhydrase inhibitors include acetazolamide, methazolamide, dorzolamide, brinzolamide, dichlorphenamide, sultiame, and topiramate. Topiramate is the active pharmaceutical ingredient in EPRONTIA® (topiramate) oral solution, which is indicated as an initial monotherapy for the treatment of partial-onset or primary generalized tonic-clonic seizures and as adjunctive therapy for the treatment of partial-onset seizures, primary generalized tonic-clonic seizures, or seizures associated with Lennox-Gastaut syndrome; and for preventive treatment of migraine.

Topiramate is a lactam containing compound and chemically described as 2,3:4,5-Di-O-isopropylidene-β-D-fructopyranose sulfamate and has the molecular formula $C_{12}H_{21}NO_8S$ and a molecular weight of 339.36. The chemical structure of topiramate is:

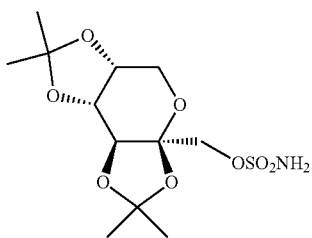

V K Parmar, R H Parikh, and R J Patel, *HPTLC Method for Estimation of Topiramate in Solubility Studies, Diffusion Studies, Plasma, Brain Homogenate and Pharmaceutical Formulation. Journal of Chromatographic Science*, 2016, Vol. 54, No. 7, 1105-1114 ("Parmar et al.") teaches, in its Table III, the solubility of topiramate in various oils, surfactants, and cosurfactants. That table is reproduced in below Table I, and as can be seen reports that the solubility of topiramate in polyethylene glycol ("PEG") 400 is 148.9±3.5 mg/ml and that the solubility of topiramate in glycerol is 8.3±0.2 mg/ml.

TABLE 1

Topiramate solubility in various oils, surfactants, and cosurfactants

| Sr. No. | Vehicle | Name of ingredient | Topiramate Solubility (mg/mL) |
|---|---|---|---|
| 01 | Oil | Capmul MCM C-8 | 62.5 ± 3.9 |
| | | Capmul MCM EP | 61.4 ± 3.8 |
| | | Aconon C-30 | 50.7 ± 3.5 |
| | | Captex 355 | 14.5 ± 0.8 |
| | | Ethyl Oleate | 6.7 ± 0.3 |
| | | Oleic Acid | 0.1 ± 0.1 |
| | | IPM | 6.7 ± 0.4 |
| | | Sesfol 218 | 53.6 ± 2.6 |
| 02 | Surfactant | Tween 80 | 84.2 ± 3 |
| | | Tween 20 | 142.8 ± 6.4 |
| | | Cremophor EL | 78 ± 2.1 |
| | | Cremophor RH-40 | 46 ± 2.7 |
| 03 | Cosurfactant | Carbitol | 355.6 ± 29.2 |
| | | PEG 200 | 169.6 ± 2.3 |
| | | PEG 400 | 148.9 ± 3.5 |
| | | Glycerol | 8.3 ± 0.2 |

SUMMARY

Certain embodiments of the present disclosure provide liquid pharmaceutical formulations, suitable for oral administration, that consist of, or consist essentially of, a therapeutically effective amount of topiramate (e.g., about 4% w/w, about 6% w/w, about 8.5% w/w topiramate, or ranges therebetween) and either: (a) 10% w/w polyethylene glycol ("PEG") 400 and a quantity of glycerol, from 72.5% w/w to 86% w/w, that brings the formulations to 100% w/w, from 25 mg/ml to 70 mg/ml of the topiramate being, at room temperature, in the solution phase of the formulations; (b) 15% w/w PEG 400 and a quantity of glycerol, from 67.5% w/w to 81% w/w, that brings the formulations to 100% w/w, from 32.5 mg/ml to 70 mg/ml of the topiramate being, at room temperature, in the solution phase of the formulations; (c) 20% w/w PEG 400 and a quantity of glycerol, from 62.5% w/w to 76% w/w, that brings the formulations to 100% w/w, from 40 mg/ml to 70 mg/ml of the topiramate being, at room temperature, in the solution phase of the formulations, or (d) 25% w/w PEG 400 and a quantity of glycerol, from 57.5% w/w to 69% w/w, that brings the formulation to 100% w/w, wherein from 47.5 mg/ml to 70 mg/ml of the topiramate is, at room temperature, in the solution phase of the formulations. Some of such formulations further contain: from 0.1% w/w to 2.0% w/w of a sweetener (e.g., sucrose) and/or from 0.01% w/w to 0.1% of a flavorant (e.g., a berry).

Certain embodiments of the present disclosure provide liquid pharmaceutical formulations, suitable for oral administration, that consist of, or consist essentially of, 50 mg/ml topiramate (e.g., about 4% w/w topiramate) and either: (a) 10% w/w PEG 400 and a quantity of glycerol, from 72.5% w/w to 86% w/w, that brings the formulations to 100% w/w, from 25 mg/ml to 70 mg/ml of the topiramate being, at room temperature, in the solution phase of the formulations; (b) 15% w/w PEG 400 and a quantity of glycerol, from 67.5% w/w to 81% w/w, that brings the formulations to 100% w/w, from 32.5 mg/ml to 70 mg/ml of the topiramate being, at room temperature, in the solution phase of the formulations; (c) 20% w/w PEG 400 and a quantity of glycerol, from 62.5% w/w to 76% w/w, that brings the formulations to 100% w/w, from 40 mg/ml to 70 mg/ml of the topiramate being, at room temperature, in the solution phase of the formulations, or (d) 25% w/w PEG 400 and a quantity of glycerol, from 57.5% w/w to 71% w/w, that brings the formulation to 100% w/w, wherein from 47.5 mg/ml to 70 mg/ml of the topiramate is, at room temperature, in the solution phase of the formulations. Some of such formulations contain 50 mg/ml topiramate, 75 mg/ml topiramate, or 100 mg/ml topiramate. Some of such formulations contain 4.2% w/w topiramate, 6.3% w/w topiramate, or 8.3% w/w topiramate. Some of such formulations further contain: from 0.1% w/w to 2.0% w/w of a sweetener (e.g., sucrose) and/or from 0.01% w/w to 0.1% of a flavorant (e.g., a berry). One of such formulations contains 6.3% w/w topiramate, 25%, w/w PEG 400, 0.2% w/w flavorant berry 807.0246U, 0.8% sweetener sucralose, and balance glycerol.

Certain embodiments of the disclosure provide methods of making formulations of the present disclosure that involve the steps of mixing the glycerol, the PEG 400, and the topiramate to form a suspension or clear solution. In such embodiments, when a suspension results from the mixing, the formulation can be heated to between 40° C. and 50° C., 55° C., 60° C., 65° C., 70° C., 75° C., 80° C., 85° C., 90° C., 95° C., 100° C., or 125° C., until a clear solution is obtained. Also in such embodiments, the topiramate can be mixed with the PEG 400 to form a suspension or a clear solution and then the glycerol can be mixed with the suspension or the solution of PEG 400 and glycerol. Further in such embodiments, when a suspension results from mixing the topiramate and the PEG 400, the mixture of the topiramate and the PEG 400 can be heated to between 40° C. and 50° C., 55° C., 60° C., 65° C., 70° C., 75° C., 80° C., 85° C., 90° C., 95° C., 100° C., or 125° C. or ranges between those temperatures until a clear solution is obtained or the mixture of the topiramate, PEG 400, and the glycerol can be heated to between 40° C. and 50° C., 55° C., 60° C., 65° C., 70° C., 75° ° C., 80° ° C., 85° C., 90° C., 95° C., 100° ° C., or 125° C. or ranges between those temperatures, until a clear solution is obtained.

Certain embodiments of the disclosure provide methods of treating one or more of conditions: (i) partial-onset tonic-clonic seizures, (ii) primary generalized tonic-clonic seizures, or (iii) seizures associated with Lennox-Gastaut syndrome, comprising orally administering a formulation of the disclosure to a subject presenting one or more of conditions (i), (ii), and (iii).

Certain embodiments of the present disclosure provide liquid pharmaceutical formulations, suitable for oral administration, that comprise a therapeutically effective amount of topiramate and either: (a) about 15% w/w PEG 400 and about 85% w/w glycerol, wherein 32.5 mg/ml, 35 mg/ml, 37.5 mg/ml, 40 mg/ml, 42.5 mg/ml, 45 mg/ml, 47.5 mg/ml to 50 mg/ml of the topiramate is in the solution phase of the formulation, at room temperature; (b) about 17.5% w/w PEG 400 and about 82.5% w/w glycerol, wherein from 35 mg/ml, 37.5 mg/ml, 40 mg/ml, 42.5 mg/ml, 45 mg/ml, or 47.5 mg/ml to 50 mg/ml of the topiramate is in the solution phase of the formulation, at room temperature; (c) about 20% w/w PEG 400 and about 80% w/w glycerol, wherein from 40 mg/ml, 42.5 mg/ml, 45 mg/ml, or 47.5 mg/ml to 50 mg/ml of the topiramate is in the solution phase of the formulation, at room temperature; (d) about 22.5% w/w PEG 400 and about 77.5% w/w glycerol, wherein from 42.5 mg/ml, 45 mg/ml, or 47.5 mg/ml to 50 mg/ml of the topiramate is in the solution phase of the formulation, at room temperature; or about 25% w/w PEG and about 75% w/w glycerol, wherein from 45 mg/ml or 47.5 mg/ml to 50 mg/ml of the topiramate is in the solution phase of the formulation, at room temperature. In such formulations, the concentration of topiramate is about 50 mg/ml. Some of such formulations contain about 20% w/w PEG 400 and about 80% w/w glycerol and possess from either 42.5 mg/ml, 45 mg/ml, or 47.5 mg/ml to 50 mg/ml of the topiramate in the solution phase of the formulation. Some of such formulations further contain: from 0.1% w/w to 2.0% w/w of a sweetener (e.g., sucrose) and/or from 0.01% w/w to 0.1% of a flavorant (e.g., a berry).

Certain embodiments of the disclosure provide methods of making formulations of the disclosure that involve the steps of mixing the glycerol, the PEG 400, and the topiramate to form a suspension or clear solution. In some of such embodiments, when a suspension results from the mixing, the formulation is heated to between 40° C. and 50° C., 55° C., 60° C., 65° C., 70° C., 75° C., 80° C., 85° C., 90° C., 95° C., 100° C., or 125° C., until a clear solution is obtained. In some of such methods, the topiramate is mixed with the PEG 400 to form a suspension or a clear solution and then the glycerol is mixed with the suspension or the solution of the PEG 400 and glycerol. In some of such methods, when a suspension results from mixing the topiramate and the PEG 400, the mixture of the topiramate and the PEG 400 is heated to between 40° C. and either 50° C., 55° C., 60° ° C., 65° C., 70° C., 75° C., 80° C., 85° C., 90° C., 95° C., 100° C., 125° C., 150° C., 175° C., 200° C., 225° C., 250° C., 275° C., 300° C., 325° C., 350° C., 375° C., 400° C., 425° C., 450° C., 475° C., or 500° C., until a clear solution is obtained or the mixture of the topiramate, PEG 400, and the glycerol is heated to between 40° C. and 50° C., 55° C., 60° C., 65° C., 70° C., 75° C., 80° C., 85° C., 90° C., 95° C., 100° C., or 125° C., until a clear solution is obtained.

Certain embodiments of the disclosure provide methods of treating partial-onset tonic-clonic seizures, primary generalized tonic-clonic seizures, and/or seizures associated with Lennox-Gastaut syndrome, comprising orally administering a formulation of the present disclosure to a subject presenting one or more of such conditions.

DETAILED DESCRIPTION

The present disclosure provides liquid pharmaceutical formulations of topiramate that are suitable for oral administration. Such formulations exhibit advantageous topiramate solubilities that are surprisingly greater than the maximum solubilities for topiramate taught by the prior to the instant disclosure, in the excipients PEG 400 and glycerol. Prior-art-taught maximum topiramate solubilities are calculated by multiplying the prior-art-taught solubility of topiramate in PEG 400 alone or in glycerol alone by, respectively, the percentages of PEG 400 and glycerol in a hypothetical formulation; and then adding together the contributions of topiramate solubility for each of PEG 400 and glycerol, to arrive at the prior-art-taught maximum topiramate solubility for the applicable hypothetical formulation. In comparison, observed topiramates solubilities exhibited by formulations of the instant disclosure surprisingly and advantageously exhibit greater than those calculated therefore.

Formulations of the disclosure are useful for treating treatment of glaucoma, altitude sickness, ulcers, idiopathic intracranial hypertension, osteoporosis, type II diabetes, tobacco dependence, obesity, eating disorders (e.g., binge eating and antipsychotic-induced weight gain), neurological disorders (e.g., depression, mania, bipolar disorder, and borderline personality disorder), migraine, partial-onset or primary generalized tonic-clonic seizures, and partial-onset seizures, primary generalized tonic-clonic seizures, or seizures associated with Lennox-Gastaut syndrome; and for preventive treatment of migraine.

Formulations as disclosed herein can "comprise" a list of ingredients, such list then being open to inclusion of further unspecified ingredients. Alternatively, formulations as disclosed herein can "consist of" a list of ingredients, meaning that the formulations include only the listed ingredients. Or, formulations as disclosed herein can "consist essentially of" the listed ingredients, meaning that the formulations include all of the listed ingredients, and may include as well any further ingredients that do not materially affect the utility of the formulation. Such utility for the purposes of the present disclosure is maintenance of a high concentration of topiramate in a solution phase in a liquid formulation.

Formulations as disclosed herein may consist of topiramate, or a pharmaceutically acceptable salt thereof, glycerol and a PEG as these are described, and in the proportions disclosed, herein below. Formulations as disclosed herein may consist of topiramate or a pharmaceutically acceptable salt thereof, glycerol and a polyethylene glycol (PEG) as these are described, and in the proportions disclosed, herein below, and further any one or more of a flavorant, a pH adjusting agent and/or a buffer, a polymer, a surfactant, a tonicity agent and a preservative, as these are described, and in the proportions disclosed, herein below.

In some formulations of the disclosure, the proportion, of the total amount of topiramate in the formulation, that is in the solution phase thereof can be 35%, 40%, 45%, 50%, 55%, 60%, 65%, 70%, 75%, 80%, 85%, 90%, 95%, 96% 97%, 98%, 99%, or 100% or ranges between two of those percentages.

In some embodiments, formulations of the present disclosure contain topiramate, at concentrations in the overall formulation, of 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, 100 mg/ml, 110 mg/ml, 120 mg/ml, 130 mg/ml, 140 mg/ml, or 150 mg/ml or ranges between any two of those concentrations.

In some embodiments, formulations of the present disclosure contain topiramate, at concentrations in the solution phase of the formulation of 20 mg/ml, 22.5 mg/ml, 25 mg/ml, 27.5 mg/ml, 30 mg/ml, 32.5 mg/ml, 35 mg/ml, 37.5 mg/ml, 40 mg/ml, 40 mg/ml, 42.5 mg/ml, 45 mg/ml, 47.5 mg/ml, 50 mg/ml, 52.5 mg/ml, 55 mg/ml, 57.5 mg/ml, 60 mg/ml, 62.5 mg/ml, 65 mg/ml, 67.5 mg/ml, 70 mg/ml, 72.5 mg/ml, 75 mg/ml, 77.5 mg/ml, 80 mg/ml, 82.5 mg/ml, 85 mg/ml, 87.5 mg/ml, 90 mg/ml, 92.5 mg/ml, 95 mg/ml, 97.5 mg/ml, or 100 mg/ml, or ranges between two of those concentrations.

In some embodiments, a formulation of the disclosure can consist of the topiramate, PEG, and glycerine. In some embodiments, a formulation of the disclosure can consist of the topiramate, PEG, and glycerol and one or more of a sweetener, flavorant, polymer, surfactant, tonicity agent and preservative as described below.

PEGs useful in formulations of the disclosure include those having a molecular weight of 200, 300, 400, 500, 600, 1000, 2000, 3000, 5000, or 8000 or in a range between any two of those molecular weights. Formulation of the disclosure may comprise PEG in weight to weight proportions of the overall formulation of 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, or 95% w/w or in a range between any two of those PEG proportions. The formulations may comprise combinations of PEG, in amounts that individually or in aggregate achieve(s) the stated tonicity weight to volume proportions.

Glycerols useful in formulations of the disclosure include glycerol USP Grade (1,2,3-Propanetriol), a colorless, odorless liquid available at a minimum 96.0% or a minimum 99.5% glycerol by assay. Commercially available glycerols include 99.9% glycerol by Puratin, 99.7% glycerol by Optim, 100% glycerol by JT Baker, 99.5% glycerol by MP Biomedicals, 99.4% glycerol by Honeywell, 99.8% glycerol by VWR Scientific, 99% glycerol by Spectrum, 100% glycerol by Millipore Sigma, 99% glycerol by Bean Town Chemical, 99.9% glycerol by ThermoFisher Scientific Chemicals, 99.8% glycerol by Arcos Chemicals, 99.8% glycerol by VWR International. Also useful in formulations of the disclosure are glycerol esters that include glycerol 2 ethyl hexyl oleate, glycerol trioleate, glyceryl dioleate, glyceryl monooleate, and glyceryl monotallate. Formulation of the disclosure may comprise glycerol in weight to weight proportions of the overall formulation of 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, 95% w/w or in a range between two of those proportions.

In some embodiments, formulations of the disclosure can include a sweetener. Sweeteners useful in the formulations of the present disclosure include acesulfame-K, advantame, alitame, aspartame, brazzein, carrelame, curculin, cyclamic acid, corn syrup (e.g., high fructose corn syrup), cyclamate, dihydrochalchone, erythritol, fructose, galactose, glucose, glycerin, glycine, glycyrrhizic acid, hydrogenated glucose syrup, hydrogenated starch hydrolysate, isomalt, lactitol, lactose, mabilin, miraculin, maltitol, maltodextrin, maltose, monatin, mannitol, mannose, mogrosides, monellin, neohesperidin, pentadin, saccharin, sorbitol, stevia glycosides, sucralose, sucrose, tagatose, tryptophan, and xylitol. The sweetener may be present in liquid pharmaceutical formulations of the disclosure in weight to weight proportions of 0.01% w/w, 0.10% w/w, 0.15% w/w, 0.20% w/w, 0.25% w/w, 0.30% w/w, 0.35% w/w, 0.40% w/w, 0.45% w/w, 0.50% w/w, 0.55% w/w, 0.60% w/w, 0.65% w/w, 0.70% w/w 0.75% w/w, 0.80% w/w, 0.85% w/w, 0.90% w/w, 0.95% w/w, 1% w/w, 1.5% w/w, 2% w/w, 2.5% w/w, 3% w/w, 3.5% w/w, 4% w/w, 4.5% w/w, 5% w/w, 6% w/w, 7% w/w, 8% w/w, 9% w/w, or 10% w/w or a range between any two of those proportions. The formulations may comprise combinations of sweeteners, in amounts that individually or in aggregate achieve(s) the stated weight to weight proportions.

In some embodiments, formulations of the disclosure can include a flavorant. Flavorants useful in the formulations of the present disclosure include chocolate, vanilla, caramel, orange, lemon, lime, strawberry, raspberry, blueberry, cherry, cinnamon, and nutmeg. The flavorant may be present in liquid pharmaceutical formulations of the disclosure in weight to weight proportions of 0.01% w/w, 0.10% w/w, 0.15% w/w, 0.20% w/w, 0.25% w/w, 0.30% w/w, 0.35% w/w, 0.40% w/w, 0.45% w/w, 0.50% w/w, 0.55% w/w, 0.60% w/w, 0.65% w/w, 0.70% w/w 0.75% w/w, 0.80% w/w, 80.5% w/w, 0.90% w/w, 0.95% w/w, 1% w/w, 1.5% w/w, 2% w/w, 2.5% w/w, 3% w/w, 3.5% w/w, 4% w/w, 4.5% w/w, 5% w/w, 6% w/w, 7% w/w, 8% w/w, 9% w/w, or 10% w/w or in a range between two of those proportions. The formulations may comprise combinations of flavorant, in amounts that individually or in aggregate achieve(s) the stated weight to weight proportions.

In some embodiments, formulations of the disclosure can contain a pH adjusting agent and/or a buffer. Acidic pH adjusting agents useful in formulations of the disclosure include fumaric acid, formic acid, acetic acid, trichloroacetic acid, benzoic acid, oxalic acid, hydrofluoric acid, hydrogen sulfide, nitrous acid, sulfurous acid, phosphoric acid, and combinations thereof. Alkaline pH adjusting useful in formulations of the disclosure include sodium hydroxide, potassium hydroxide, calcium hydroxide, ammonium carbonate, ammonium hydroxide, ethanolamine, and trolamine. Buffers useful in formulations of the disclosure include acetic acid, sodium acetate, benzoic acid, sodium benzoate, boric acid, sodium borate, citric acid, sodium citrate, sodium phosphate, monobasic sodium phosphate, dibasic sodium phosphate, potassium phosphate, monobasic potassium phosphate, dibasic potassium phosphate, sodium acetate, lactic acid, a tartaric acid, sodium tartrate, sodium bicarbonate, sodium carbonate, tris(hydroxymethyl)aminomethane ("TRIS"), or a combination thereof. In such formulations, the buffer and/or pH adjusting agent are present in the formulations in amounts, alone or together, that are sufficient to cause the formulation to have a pH of from 6 to 11, for example pH 6, pH 6.1, pH 6.2, pH 6.3, pH 6.4, t pH 6.5, pH 6.6, pH 6.7, pH 6.8, pH 6.9, pH 7, pH 7.1, pH 7.2, pH 7.3, pH 7.4, pH 7.5, pH 7.6, pH 7.7, pH 7.8, pH 7.9, pH 8, pH 8.1, pH 8.2, pH 8.3, pH 8.4, pH 8.5, pH 8.6, pH 8.7, pH 8.8, pH 8.9, pH 9, pH 9.1, pH 9.2, pH 9.3, pH 9.4, pH 9.5, pH 9.6, pH 9.7, pH 9.8, pH 9.9, pH 10, pH 10.1, pH 10.2, pH 10.3, pH 10.4, pH 10.5, pH 10.6, pH 10.7, pH 10.8, pH 10.9, or pH 11 or in a range between two of those pH values.

In some embodiments, formulations of the present disclosure are pourable. The viscosities of such formulations can range from 1 centipoise ("cps") (i.e., the viscosity of water at room temperature) to 25,000 cps (i.e., the viscosity of chocolate syrup at room temperature); and exemplary particular viscosities of formulations of the disclosure include 1 cps, 25 cps, 50 cps, 75 cps, 100 cps, 150 cps, 200 cps (about the viscosity of maple syrup at room temperature), 250 cps, 300 cps, 400 cps, 500 cps, 600 cps, 700 cps, 800 cps, 900 cps, 1000 cps (about the viscosity of glycerin at room temperature), 1100 cps, 1200 cps, 1300 cps, 1400 cps, 1500 cps, 1600 cps, 1700 cps, 1800 cps, 1900 cps, 2000 cps, 2100 cps, 2200 cps, 2300 cps, 2400 cps, 2500 cps, 2600 cps, 2700 cps, 2800 cps, 2900 cps, 3000, 3500 cps, 4000 cps, 4500 cps, 5000 cps, 6000 cps, 7000 cps, 8000 cps, 9000 cps, 10,000 cps, 12,500 cps, 15,000 cps, 17,500 cps, 20,000, cps 22,500 cps, 25,000 cps (about the viscosity of chocolate syrup at room temperature), 27,500 cps, 30,000, cps as well as in a range between any two of said viscosities.

In some embodiments, formulations of the disclosure can contain a polymer. Non-ionic polymers useful in certain formulations of the disclosure include hydroxyethyl cellulose, hydroxypropylmethyl cellulose, methyl cellulose, carboxymethyl cellulose, polyvinyl pyrrolidone, and polyvinyl alcohol. Ionic polymers useful in certain formulations of the disclosure include polyacrylates (e.g., carbopols and carbomers), alginates, chitosans, hyaluronic acid, and xanthan gum. Such ionic and/or nonionic polymers may be present in formulations of the disclosure in weight to weight proportions of the overall formulation of 0.001% w/w, 0.005% w/w, 0.01% w/w, 0.05% w/w, 0.1% w/w, 0.25% w/w, 0.5% w/w, 0.75% w/w, 1.0% w/w, 1.25% w/w, 1.5% w/w, 1.75% w/w, 2.0% w/w, 2.25% w/w, 2.5% w/w, 2.75% w/w, 3.0% w/w, 3.25% w/w, 3.5% w/w 3.75% w/w, 4.0% w/w, 4.25% w/w, 4.5% w/w, 4.75% w/w, 5.0% w/w, 6.0% w/w, 7.0% w/w, 8.0% w/w, 9.0% w/w, or 10.0% w/w or in a range between two of those proportions. The formulations may comprise combinations of polymers, in amounts that individually or in aggregate achieve(s) the stated proportions.

In some embodiments, formulations of the disclosure contain a surfactant. Surfactants useful in certain formulations of the disclosure include sodium lauryl sulfate, docusate sodium, phosphatidylcholine, lecithin, betaines, tyloxapol, polyoxyethylene sorbitan esters, such as polysorbate 20, polysorbate 60, and polysorbate 80; polyethoxylated castor oils, such as cremaphor, polyethoxylated hydrogenated castor oils, such as HCO-40; and poloxamers. Such surfactants may be present in formulations of the disclosure in weight to weight proportions of the overall formulation of 0.001% w/w, 0.005% w/w, 0.01% w/w, 0.05% w/w, 0.1% w/w, 0.2% w/w, 0.3% w/w, 0.4% w/w, 0.5% w/w, 0.6% w/w, 0.7% w/w, 0.8% w/w, 0.9% w/w, 1.0% w/w, 1.1% w/w, 1.2% w/w, 1.3% w/w, 1.4% w/w, 1.5% w/w, 1.6% w/w, 1.7% w/w, 1.8% w/w, 1.9% w/w, 2.0% w/w, 3.0% w/w, 4.0% w/w, or 5.0% w/w or a range between two of those proportions. The formulations may comprise combinations of surfactants, in amounts that individually or in aggregate achieve(s) the stated weight to weight proportions.

In some embodiments, formulations of the disclosure can contain a tonicity agent. Ionic tonicity agents useful in certain formulations of the disclosure include calcium chloride, magnesium chloride, potassium chloride, sodium chloride, sodium sulfate, and combinations thereof. Nonionic tonicity agents useful in the formulations described herein include mannitol, sorbitol, xylitol, erythritol, lactitol, maltitol, isomalt, and combinations thereof. The formulations may comprise tonicity agent in weight to weight proportions of the overall formulation of 0.001% w/w, 0.005% w/w, 0.01% w/w, 0.05% w/w, 0.1% w/w, 0.2% w/w, 0.3% w/w, 0.4% w/w, 0.5% w/w, 0.6% w/w, 0.7% w/w, 0.8% w/w, 0.9% w/w, 1.0% w/w, 1.1% w/w, 1.2% w/w, 1.3% w/w, 1.4% w/w, 1.5% w/w, 1.6% w/w, 1.7% w/w, 1.8% w/w, 1.9% w/w, 2.0% w/w, 3.0% w/w, 4.0% w/w, or 5.0% w/w or a range between two of those proportions. The formulations may comprise combinations of tonicity agent, in amounts that individually or in aggregate achieve(s) the stated weight to weight proportions.

In some embodiments, formulations of the disclosure can contain water. The formulations may comprise water in weight to weight proportions of the overall formulation of 0.001% w/w, 0.005% w/w, 0.01% w/w, 0.05% w/w, 0.1% w/w, 0.25% w/w, 0.5% w/w, 0.75% w/w, 1.0% w/w, 1.25% w/w, 1.5% w/w, 1.75% w/w, 2.0% w/w, 2.25% w/w, 2.5% w/w, 2.75% w/w, 3.0% w/w, 3.25% w/w, 3.5% w/w 3.75% w/w, 4.0% w/w, 4.25% w/w, 4.5% w/w, 4.75% w/w, and 5.0% w/w, 5.5% w/w, 6.0% w/w, 6.5% w/w, 7.0% w/w, and 7.5% w/w, 8.0% w/w, 8.5% w/w, 9.0% w/w, 9.5% w/w, or 10.0% w/w or in a range between two of those proportions.

In some embodiments, formulations of the disclosure can contain a preservative. Preservatives useful in certain formulations of the disclosure include dibutylhydroxytoluene, benzalkonium chloride, benzyl alcohol, borates, parabens, cresols, benzoic acid, phenol, sorbic acid, benzethonium chloride, sodium chlorite and combinations thereof. The formulations may comprise preservative in weight to weight proportions of the overall formulation of 0.001% w/w, 0.005% w/w, 0.01% w/w, 0.05% w/w, 0.1% w/w, 0.25% w/w, 0.5% w/w, 0.75% w/w, 1.0% w/w, 1.25% w/w, 1.5% w/w, 1.75% w/w, 2.0% w/w, 2.25% w/w, 2.5% w/w, 2.75% w/w, 3.0% w/w, 3.25% w/w, 3.5% w/w 3.75% w/w, 4.0% w/w, 4.25% w/w, 4.5% w/w, 4.75% w/w, or 5.0% w/w or in a range between two of those proportions. The formulations may comprise combinations of preservatives, in amounts that individually or in aggregate achieve(s) the stated weight to weight proportions.

In any method for preparing a liquid formulation of topiramate as disclosed herein, if a suspension results from mixing of the topiramate with the glycerol, polyethylene glycol or mixture of them, the formulation can be heated to from 40° C. or above and not in excess of a temperature at which topiramate, PEG 400, and/or glycerol undergo thermal degradation such as 50° ° C., 55° ° C., 60° C., 65° C., 70° C., 75° C., 80° C., 85° C., 90° C., 95° C., 100° C., or 125° C., until a solution is obtained. The formulation is then preferably cooled to room temperature, a temperature of 25° C.±2° C.

EXAMPLES

Aspects of embodiments of the present disclosure may be further understood in light of the following examples, which should not be construed as limiting in any way. Objectives of the solubility and viscosity studies of the present disclosure were to evaluate the extent of topiramate solubility in a variety of liquid formulations.

Example 1

Topiramate solubility. Liquid topiramate formulations 037C-DS1, 037C-DS2, 037C-DS3 037C-DS4, 037C-DS5, and 037C-DS6 were prepared with the ingredients set forth in Tables 1.1a and 1.1b and were studied in the topiramate solubility experimental protocols described in this Example 1.

TABLE 1.1a

Topiramate formulations 037C-DS1-3

| Ingredient | 037C-DS1 % w/w | 037C -DS2 % w/w | 037C-DS3 % w/w |
|---|---|---|---|
| Topiramate | 6.3 (75 mg/ml) | 6.3 (75 mg/ml) | 6.3 (75 mg/ml) |
| PEG 400 | 20.8 | 25 | 29.2 |
| Glycerol | q.s. 100%~72.9% | q.s. 100%~68.8 | q.s. 100%~64.6 |

TABLE 1.1b

Topiramate formulations 037C-DS4-6

| Ingredient | 037C-DS4 (% w/w) | 037C -DS5 (% w/w) | 037C-DS6 (% w/w) | 037-DS7 (% w/w) |
|---|---|---|---|---|
| Topiramate | 8.3 (100 mg/ml) | 8.3 (100 mg/ml) | 8.3 (100 mg/ml) | 4.2 (50 mg/ml) |
| PEG 400 | 20.8 | 25 | 29.2 | 16.7 |
| Glycerol | q.s. 100%~70.8 | q.s. 100%~66.7 | q.s. 100%~62.5 | q.s. 100%~79.1 |

Topiramate batch manufacture. Formulations 037C-DS1, 037C-DS2, 037C-DS3, 037C-DS4, 037C-DS5, 037C-DS6, and 037-DS7 were made as follows. At room temperature (i.e., 25° C.±2° C.) the amounts of topiramate, PEG 400, and glycerol required for planned bulk batch size to be manufactured (e.g., for purposes of analyzing each formulation in the topiramate HPLC assay at the specified time points) were independently weighed on a laboratory scale. Such amount of the PEG 400 was transferred to a stainless-steel vessel, to which the topiramate was slowly added under continuous stirring at room temperature (i.e., 25° C.±2° C.). At this stage, formulations 037C-DS1, 037C-DS2, 037C-DS3, and 037-DS7 were clear whereas formulations 037C-DS4, 037C-DS5, and 037C-DS6 were cloudy. To the resultant liquids, the glycerol was added under continued stirring at room temperature (i.e., 25° C.±2° C.) to form the bulk formulations. The bulk formulations were subsequently stored at room temperature (i.e., 25° C.±2° C.). Formulations 037C-DS1, 037C-DS2, 037C-DS3, and 037-DS7 remained clear and formulations 037C-DS4, 037C-DS5, and 037C-DS6 remained cloudy.

Topiramate HPLC analytical testing. HPLC analytical testing (see infra) of formulations 037C-DS1, 037C-DS2, 037C-DS3, 037C-DS4, 037C-DS5, and 037C-DS6 was conducted at 0, 1, 2 and 3 days after batch manufacture, 10 ml of each bulk formulation was taken and centrifuged at 5000 rpm for 20 minutes, then the supernatant was analyzed for topiramate content by the methods described below.

The analytical methods and sampling steps performed on formulations 037C-DS1, 037C-DS2, 037C-DS3, 037C-DS4, 037C-DS5, and 037C-DS6 were conducted at room temperature (25° C.±2° C.) and as set forth in Table 1.2.

TABLE 1.2

| Time point | Analytical methods and sampling steps |
|---|---|
| $T_{0\ day}$ | a. 10 ml samples were collected from each of the bulk formulations 037C-DS1, 037C-DS2, 037C-DS3, 037C-DS4, 037C-DS5, and 037C-DS6, promptly after manufacture.<br>b. The topiramate HPLC assay was performed on each sample collected in $T_{0\ day}$ step a. The topiramate concentration (in mg/ml) of each sample was determined. |
| $T_{1\ day}$ | a. 10 ml samples were collected from each of the bulk formulations 037C-DS1, 037C-DS2, 037C-DS3, 037C-DS4, 037C-DS5, and 037C-DS6, 24 hours after manufacture.<br>b. The topiramate HPLC assay was performed on each sample collected in $T_{1\ day}$ step a. The topiramate concentration (in mg/ml) of each sample was determined. |
| $T_{2\ days}$ | a. 10 ml samples were collected from each of the bulk formulations 037C-DS1, 037C-DS2, 037C-DS3, 037C-DS4, 037C-DS5, and 037C-DS6, 48 hours after manufacture.<br>b. The topiramate HPLC assay was performed on each sample collected in $T_{2\ days}$ step a. The topiramate concentration (in mg/ml) of each sample was determined. |

The solutions, standards, and samples used in the topiramate assay analytical methods of the present disclosure were as described in Table 1.2.

TABLE 1.2

Topiramate assay solutions

| | |
|---|---|
| Water | HPLC grade (e.g., MilliQ or equivalent) |
| Column wash | HPLC grade acetonitrile (e.g., Merck or JT Baker) and water (60:40 v/v) |
| Mobile phase | Acetonitrile and water (60:40 v/v) |
| Diluent | Acetonitrile and water (50:50) |
| Assay standard solution | 2 mg/mL topiramate RS in mobile phase |
| Assay sample solution | 2 mg/mL topiramate RS in mobile phase |
| Assay system suitability solution | 0.02 mg/mL each of fructose RS and USP topiramate related compound A RS in the sample solution |

The chromatographic conditions for the topiramate high performance liquid chromatography ("HPLC") assay employed in the present disclosure were as forth in Table 1.3.

TABLE 1.3

Topiramate Assay HPLC system

| Chromatographic parameters | Equipment and/or conditions |
|---|---|
| System | HPLC-RI |
| Detector | Refractive index |
| Elution mode | Isocratic |
| Column | 4.6-mm × 25-cm; 5-μm packing L1 (Inertsil ODS 250 × 4.6 mm, 5 μm) |
| Column temperature | 50° C. |
| Sampler temperature | 25° C. |
| Detector temperature | 55° C. |
| Flow Rate | 0.6 ml/min |
| Polarity | Positive |
| Injection volume | 50 μl |
| Topiramate retention time | 12 to 13 minutes |
| Run Time | Not less than 3 times the topiramate retention time |

Standard solutions I & II preparation. 50 mg of topiramate was weighed and transferred into a 50 ml volumetric flask, to which 20 ml diluent was added and sonicated until dissolved. The resultant solution was mixed well and diluted with the same diluent until 1000 μg/ml of topiramate was attained. Preparation of standard solution II was the same as for standard solution I.

Sample solution preparation. 1.0 g of sample supernatant was weighed and transferred into 25 ml volumetric flask, to which 15 ml diluent was added, vigorously shaken for 5 minutes, and sonicated for 5 minutes. The resultant solution was with the same diluent until 1000 μg/ml of topiramate was achieved. Note: topiramate HPLC assay samples were prepared in duplicate and run through the HPLC assay. Their average value was reported.

Topiramate HPLC assay procedure. The HPLC system was equilibrated with mobile phase. Iterative injections of diluent were made until a clean and reproducible baseline was achieved. The chromatograms were recorded and any peak eluting at the retention time of major peaks identified. Five replicate injections of topiramate standard solution I and two replicate injections of topiramate standard solution II were made and chromatograms recorded. The sample solution was injected (in duplicate) and topiramate content calculated in terms of percentage with equations provided in Table 1.4.

The equation employed to calculate percent assay for topiramate in the samples of the formulations of the present disclosure are set forth in Table 1.4.

TABLE 1.4

Topiramate HPLC assay equations

Assay for topiramate $= \frac{Aspl}{Astd} \times \frac{Wstd(\text{mg})}{50 \text{ mL}} \times \frac{25 \text{ mL}}{Wspl(\text{mg})} \times \frac{P(\%)}{100} \times \text{Wt./mL}$ Percent assay $\% \text{ Assay} = \frac{\text{Assay}(\text{mg/ml})}{LC(\text{mg/ml})} \times 100$ Where:
Astd  Average area response of five replicate injections for topiramate in standard solution I
Aspl  Average area response of topiramate obtained in the sample solution
Wstd  Weight of the topiramate working standard taken in mg
Wspl  Weight of sample in mg
P     Purity of topiramate working standard on as is basis in percentage
L     Label claim of topiramate in mg/ml
Wt/ml Weight per ml in g/ml The HPLC assay experimental results for formulations 037C-DS1, 037C-DS2, 037C-DS3, 037C-DS4, 037C-DS5, and 037C-DS6 are reported in Tables 1.5a and 1.5b.

TABLE 1.5a

| Formulation | Calculated max topiramate solubility (mg/ml) | Observed topiramate solubility (mg/ml) | | | |
|---|---|---|---|---|---|
| | | D0 | D1 | D2 | D3 |
| 037C-DS1 | 43 | 70.0 | 64.0 | 69.4 | 58.4 |
| 037C-DS2 | 50 | 71.0 | 72.4 | 70.3 | 69.1 |
| 037C-DS3 | 57 | 73.7 | 73.0 | 73.6 | 74.8 |

TABLE 1.5b

| Formulation | Calculated max topiramate solubility (mg/ml) | Observed topiramate solubility (mg/ml) | | | |
|---|---|---|---|---|---|
| | | D0 | D1 | D2 | D3 |
| 037C-DS4 | 43 | 38.0 | 36.8 | 36.9 | 34.5 |
| 037C-DS5 | 50 | 60.1 | 56.2 | 54.7 | 53.5 |
| 037C-DS6 | 57 | 98.3 | 97.8 | 98.1 | 94.9 |

The resulting concentration of soluble topiramate (i.e., the topiramate in the supernatant after centrifugation) observed and reported in tables 1.5a and 1.5b exceeds the maximum topiramate solubility calculated as taught by the prior art for all formulations of the instant disclosure, except 037C-DS4. The inventors have surprisingly and unexpectedly found in additional studies that application of a heating step to the batch manufacturing process of formulations 037-DS4, 037-DS4, and 037-DS5 significantly increases the amount of topiramate in the solution phase. In particular, the cloudy liquid topiramate suspension resultant from the addition of topiramate to PEG 400 was heated to 55° C. until a clear solution was formed. By way of example, 037-DS4 was manufactured with this additional heating step and analyzed in the analytical assay method described above and exhibited a topiramate solubility of 69 mg/ml on day 3 after manufacture (significantly greater than the 34.5 mg/ml topiramate solubility that 037-DS4 formulation exhibited on day 3 after manufacture at room temperature and without a heating step).

Formulation 037-DS7 remained a clear solution after six months of storage at room temperature.

While the foregoing specification teaches the principles of the present invention, with examples provided for the purpose of illustration, it will be understood that the practice of the invention encompasses all variations, adaptations and/or modifications as come within the scope of the following claims and their equivalents.

What is claimed is:

1. A liquid pharmaceutical formulation, suitable for oral administration, that consists of a therapeutically effective amount of topiramate and:
   (a) 10% w/w polyethylene glycol ("PEG") 400 and a quantity of glycerol, from 72.5% w/w to 86% w/w, that brings the formulation to 100% w/w, wherein from 25 mg/ml to 70 mg/ml of the topiramate is, at room temperature, in the solution phase of the formulation;
   (b) 15% w/w PEG 400 and a quantity of glycerol, from 67.5% w/w to 81% w/w, that brings the formulation to 100% w/w, wherein from 32.5 mg/ml to 70 mg/ml of the topiramate is, at room temperature, in the solution phase of the formulation;
   (c) 20% w/w PEG 400 and a quantity of glycerol, from 62.5% w/w to 76% w/w, that brings the formulation to 100% w/w, wherein from 40 mg/ml to 70 mg/ml of the topiramate is, at room temperature, in the solution phase of the formulation; or
   (d) 25% w/w PEG 400 and a quantity of glycerol, from 57.5% w/w to 71% w/w, that brings the formulation to 100% w/w, wherein from 47.5 mg/ml to 70 mg/ml of the topiramate is, at room temperature, in the solution phase of the formulation.

2. A method of making the formulation of claim 1, consisting of: mixing the PEG 400, the glycerol, and the topiramate to form a suspension or clear solution.

3. The method of claim 2, wherein when a suspension results from the mixing, the formulation is heated to between 40° C. and 100° C. until a clear solution is obtained.

4. The method of claim 2, wherein the topiramate is mixed with the PEG 400 to form a suspension or a clear solution and then the glycerol is mixed with the suspension or the clear solution of PEG 400 and topiramate.

5. The method of claim 4, wherein when a suspension results from mixing the topiramate and the PEG 400, the mixture of the topiramate and the PEG 400 is heated to between 40° C. and 100° C. until a clear solution is obtained or the mixture of the topiramate, PEG 400, and the glycerol is heated to between 40° C. and 100° C. until a clear solution is obtained.

6. A method of treating one or more of conditions: (i) partial-onset tonic-clonic seizures, (ii) primary generalized tonic-clonic seizures, or (iii) seizures associated with Lennox-Gastaut syndrome, comprising orally administering the formulation of claim 1 to a subject presenting one or more of conditions (i), (ii), and (iii).

7. A liquid pharmaceutical formulation, suitable for oral administration, that consists of about 4% w/w to about 8% w/w topiramate and:
   (a) 10% w/w PEG 400 and a quantity of glycerol, from 81% w/w to 86% w/w, that brings the formulation to 100% w/w, wherein from 25 mg/ml to 70 mg/ml of the topiramate is, at room temperature, in the solution phase of the formulation;
   (b) 15% w/w PEG 400 and a quantity of glycerol, from 76% w/w to 81% w/w, that brings the formulation to 100% w/w, wherein from 32.5 mg/ml to 70 mg/ml of the topiramate is, at room temperature, in the solution phase of the formulation;
   (c) 20% w/w PEG 400 and a quantity of glycerol, from 71% w/w to 76% w/w, that brings the formulation to 100% w/w, wherein from 40 mg/ml to 70 mg/ml of the topiramate is, at room temperature, in the solution phase of the formulation; or
   (d) 25% w/w PEG 400 and a quantity of glycerol, from 65% w/w to 69% w/w, that brings the formulation to 100% w/w, wherein from 47.5 mg/ml to 70 mg/ml of the topiramate is, at room temperature, in the solution phase of the formulation.

8. A method of making the formulation of claim 7, consisting of: mixing the glycerol, the PEG 400, and the topiramate to form a suspension or clear solution.

9. The method of claim 8, wherein when a suspension results from the mixing, the formulation is heated to between 40° C. and 100° ° C. until a clear solution is obtained.

10. The method of claim 9, wherein the topiramate is mixed with the PEG 400 to form a suspension or a clear solution and then the glycerol is mixed with the suspension or the clear solution of PEG 400 and topiramate.

11. The method of claim 10, wherein when a suspension results from mixing the topiramate and the PEG 400, the mixture of the topiramate and the PEG 400 is heated to between 40° C. and 100° C. until a clear solution is obtained or the mixture of the topiramate, PEG 400, and the glycerol is heated to between 40° C. and 100° C. until a clear solution is obtained.

12. A method of treating one or more of conditions: (i) partial-onset tonic-clonic seizures, (ii) primary generalized tonic-clonic seizures, or (iii) seizures associated with Lennox-Gastaut syndrome, comprising orally administering the formulation of claim 7 to a subject presenting one or more of conditions (i), (ii), and (iii).

13. A liquid pharmaceutical formulation, suitable for oral administration, that consists of a therapeutically effective amount of topiramate, from 0.01% w/w to 2.0% w/w of a sweetener, from 0.01% w/w to 2.0% w/w of a flavorant, or a combination the sweetener and the flavorant, and:
   (a) 10% w/w polyethylene glycol ("PEG") 400 and a quantity of glycerol, from 72.5% w/w to 86% w/w, that brings the formulation to 100% w/w, wherein from 25 mg/ml to 70 mg/ml of the topiramate is, at room temperature, in the solution phase of the formulation;
   (b) 15% w/w PEG 400 and a quantity of glycerol, from 67.5% w/w to 81% w/w, that brings the formulation to 100% w/w, wherein from 32.5 mg/ml to 70 mg/ml of the topiramate is, at room temperature, in the solution phase of the formulation;
   (c) 20% w/w PEG 400 and a quantity of glycerol, from 62.5% w/w to 76% w/w, that brings the formulation to 100% w/w, wherein from 40 mg/ml to 70 mg/ml of the topiramate is, at room temperature, in the solution phase of the formulation; or (d) 25% w/w PEG 400 and a quantity of glycerol, from 57.5% w/w to 71% w/w, that brings the formulation to 100% w/w, wherein from 47.5 mg/ml to 70 mg/ml of the topiramate is, at room temperature, in the solution phase of the formulation.

14. The formulation of claim 13, wherein the sweetener is sucrose.

15. The formulation of claim 13, wherein the flavorant is a berry.

16. The formulation of claim 13, wherein the formulation further consists of the sweetener and the flavorant, wherein the sweetener is sucrose and the flavorant is a berry.

17. A liquid pharmaceutical formulation, suitable for oral administration, that consists of about 4% w/w to about 8% w/w topiramate, and:

(a) 10% w/w PEG 400 and a quantity of glycerol, from 81% w/w to 86% w/w, that brings the formulation to 100% w/w, wherein from 25 mg/ml to 70 mg/ml of the topiramate is, at room temperature, in the solution phase of the formulation;

(b) 15% w/w PEG 400 and a quantity of glycerol, from 76% w/w to 81% w/w, that brings the formulation to 100% w/w, wherein from 32.5 mg/ml to 70 mg/ml of the topiramate is, at room temperature, in the solution phase of the formulation;

(c) 20% w/w PEG 400 and a quantity of glycerol, from 71% w/w to 76% w/w, that brings the formulation to 100% w/w, wherein from 40 mg/ml to 70 mg/ml of the topiramate is, at room temperature, in the solution phase of the formulation; or (d) 25% w/w PEG 400 and a quantity of glycerol, from 65% w/w to 69% w/w, that brings the formulation to 100% w/w, wherein from 47.5 mg/ml to 70 mg/ml of the topiramate is, at room temperature, in the solution phase of the formulation, wherein each of (a), (b), (c), and (d) further consist of: (i) from 0.01% w/w to 2.0% w/w of a sweetener, (ii) from 0.01% w/w to 2.0% w/w of a flavorant, or (iii) a combination of the sweetener and the flavorant.

18. The formulation of claim 17, wherein the sweetener is sucrose.

19. The formulation of claim 17, wherein the flavorant is a berry.

20. The formulation of claim 17, wherein the formulation consists of the sweetener and the flavorant, wherein the sweetener is sucrose and the flavorant is a berry.

* * * * *